United States Patent
Li et al.

(10) Patent No.: US 9,421,188 B2
(45) Date of Patent: *Aug. 23, 2016

(54) COMBINATION PRODUCT COMPRISING PHENTERMINE AND TOPIRAMATE, AND PREPARATION METHOD THEREOF

(71) Applicant: Institute of Pharmacology and Toxicology Academy of Military Medical Sciences P.L.A. China, Beijing (CN)

(72) Inventors: Song Li, Beijing (CN); Chunsheng Gao, Beijing (CN); Wu Zhong, Beijing (CN); Yuli Wang, Beijing (CN); Meiyan Yang, Beijing (CN); Li Shan, Beijing (CN); Xinbo Zhou, Beijing (CN); Zhibing Zheng, Beijing (CN); Xiaokui Wang, Beijing (CN)

(73) Assignee: Institute of Pharmacology and Toxicology Academy of Military Medical Sciences P.L.A. China, Beijing (CN)

( * ) Notice: Subject to any disclaimer, the term of this patent is extended or adjusted under 35 U.S.C. 154(b) by 0 days.
This patent is subject to a terminal disclaimer.

(21) Appl. No.: 14/386,148

(22) PCT Filed: Mar. 20, 2013

(86) PCT No.: PCT/CN2013/072909
§ 371 (c)(1),
(2) Date: Sep. 18, 2014

(87) PCT Pub. No.: WO2013/139266
PCT Pub. Date: Sep. 26, 2013

(65) Prior Publication Data
US 2015/0044295 A1    Feb. 12, 2015

(30) Foreign Application Priority Data

Mar. 23, 2012 (CN) .......................... 2012 1 0080568

(51) Int. Cl.
*A61K 9/50* (2006.01)
*A61K 31/357* (2006.01)
(Continued)

(52) U.S. Cl.
CPC ........... *A61K 31/357* (2013.01); *A61K 9/4808* (2013.01); *A61K 9/5047* (2013.01); *A61K 9/5078* (2013.01); *A61K 9/5084* (2013.01); *A61K 9/5089* (2013.01); *A61K 31/137* (2013.01)

(58) Field of Classification Search
None
See application file for complete search history.

(56) References Cited

U.S. PATENT DOCUMENTS

| 8,663,683 B2 | 3/2014 | Liang et al. |
| 2002/0064563 A1 | 5/2002 | Thakur et al. |

(Continued)

FOREIGN PATENT DOCUMENTS

| CN | 1646538 A | 7/2005 |
| CN | 1905857 A | 1/2007 |

(Continued)

OTHER PUBLICATIONS povidone K30 accessed online May 18, 2015 at http://www.drugs.com/inactive/povidone-k30-373.html.*

(Continued)

*Primary Examiner* — Robert A Wax
*Assistant Examiner* — Melissa Mercier
(74) *Attorney, Agent, or Firm* — Sterne, Kessler, Goldstein & Fox P.L.L.C.

(57) ABSTRACT

The present invention provides a combination product, which comprises immediate release pellet of phentermine and sustained-release pellet of topiramate, wherein the pellet of topiramate includes: a) a blank pellet core; b) an active drug layer that contains topiramate and is free of binding agent, the layer being located on surface of the blank pellet core; c) a sustained-release coating layer containing ethyl cellulose and PVP K30, the sustained-release coating layer being located on external of the active drug layer. The present invention further discloses a method for preparing the combination product.

25 Claims, 3 Drawing Sheets

(51) Int. Cl.
*A61K 31/137* (2006.01)
*A61K 9/48* (2006.01)

(56) References Cited

U.S. PATENT DOCUMENTS

| | | | |
|---|---|---|---|
| 2003/0072802 A1 | 4/2003 | Cutler | |
| 2005/0191351 A1 | 9/2005 | Kidane et al. | |
| 2005/0250944 A1 | 11/2005 | Chen | |
| 2007/0154550 A1* | 7/2007 | Arti | 424/472 |
| 2008/0118557 A1 | 5/2008 | Liang et al. | |
| 2009/0304789 A1* | 12/2009 | Najarian | A61K 31/137 424/457 |
| 2010/0215739 A1 | 8/2010 | Najarian et al. | |
| 2011/0207718 A1 | 8/2011 | Bird | |
| 2011/0287103 A1 | 11/2011 | Liang et al. | |
| 2015/0044295 A1 | 2/2015 | Li et al. | |
| 2015/0056292 A1 | 2/2015 | Li et al. | |
| 2015/0099003 A1 | 4/2015 | Li et al. | |

FOREIGN PATENT DOCUMENTS

| | | |
|---|---|---|
| CN | 1988889 A | 6/2007 |
| CN | 101035519 A | 9/2007 |
| CN | 101291662 A | 10/2008 |
| CN | 101862297 A | 10/2010 |
| CN | 102112126 A | 6/2011 |
| CN | 102112127 A | 6/2011 |
| CN | 102170874 A | 8/2011 |
| CN | 102579367 A | 7/2012 |
| CN | 1419444 A | 5/2013 |
| JP | 2001-321126 A | 11/2001 |
| JP | 2011-529923 A | 12/2011 |
| WO | WO 99/44581 A2 | 9/1999 |
| WO | WO 03/070738 A2 | 8/2003 |
| WO | WO 2005/048981 A1 | 6/2005 |
| WO | WO 2005/079748 A2 | 9/2005 |
| WO | WO 2006/009403 A1 | 1/2006 |
| WO | WO 2006/017537 A1 | 2/2006 |
| WO | WO 2007/048027 A2 | 4/2007 |
| WO | WO 2007/102714 A1 | 9/2007 |
| WO | WO 2008/027557 A2 | 3/2008 |
| WO | WO 2008/048469 A2 | 4/2008 |
| WO | WO 2009/152189 A1 | 12/2009 |
| WO | WO 2009/152190 A1 | 12/2009 |
| WO | WO 2010/015029 A1 | 2/2010 |
| WO | WO 2011/095973 A1 | 8/2011 |
| WO | WO 2011/107855 A2 | 9/2011 |
| WO | WO 2013/139209 A1 | 9/2013 |
| WO | WO 2013/139266 | 9/2013 |
| WO | WO 2013/139292 A1 | 9/2013 |

OTHER PUBLICATIONS

International Search Report (ISR) for PCT/CN2013/072909; I.A. fd: Mar. 20, 2013, mailed Jun. 27, 2013 from the State Intellectual Property Office of the P.R. China, Beijing, China
International Preliminary Report on Patentability (IPRP), Chapter I of the Patent Cooperation Treaty, including the Written Opinion for PCT/CN2013/072909; I.A. fd: Mar. 20, 2013, issued Sep. 23, 2014, from the International Bureau of WIPO, Geneva, Switzerland.
Final Office Action mailed Sep. 18, 2015 in U.S. Appl. No. 14/386,173, Li, S. et al., filed Sep. 18, 2014.
Non-Final Office Action mailed May 22, 2015 in U.S. Appl. No. 14/386,173, Li, S. et al., filed Sep. 18, 2014.
Final Office Action mailed Aug. 18, 2015 in U.S. Appl. No. 14/386,478, Li, S. et al., filed Sep. 19, 2014.
Non-Final Office Action mailed Mar. 30. 2015 in U.S. Appl. No. 14/386,478, Li, S. et al., filed Sep. 19, 2014.
Clapham, JC et al., "Anti-obesity drugs: a critical review of current therapies and future opportunities," *Pharmacol Ther* 89(1):81-121, Pergamon Press, Oxford, England (2001).
Rossato, LG et al.,"Synephrine: from trace concentrations to massive consumption in weight-loss," *Food Chem Toxicol* 49(1):8-16, Elsevier Science Ltd, Exeter, England (Jan. 2011).
Drugs.com "Povidone K30," http://www.drugs.com/inactive/povidone-k30-373.html, last accessed on Jun. 17, 2015, 4 pages.
Bowen, P., "Particle Size Distribution Measurement from Millimeters to Nanometers and from Rods to Platelets," *Journal Of Dispersion Science And Technology* 23(5):631-662, Marcel Dekker, Inc., United States (2002).
Ansel, H.C., et al., Pharmaceutical Dosage Forms and Drug Delivery Systems, 7th Ed., pp. 211, 223, 224, 232, and 233, Lippincott Williams & Wilkins, United States (1999).
Office Action mailed Dec. 18, 2015 in U.S. Appl. No. 14/386,478, Li, S., et al., filed Sep. 19, 2014.
Supplementary European Search Report and Written Opinion for European Application No. EP 13 76 3543, European Patent Office, Munich Germany, mailed on Oct. 9, 2015.
Applicant Initiated Interview Summary mailed Feb. 26, 2016 in U.S. Appl. No. 14/386,173, Li, S., et al., filed Sep. 18, 2014.
Advisory Action mailed Jan. 15, 2016 in U.S. Appl. No. 14/386,173, Li, S., et al., filed Sep. 18, 2014.
Office Action mailed Apr. 26, 2016 in U.S. Appl. No. 14/386,173, Li, S., et al., filed Sep. 18, 2014.

* cited by examiner

COMBINATION PRODUCT COMPRISING PHENTERMINE AND TOPIRAMATE, AND PREPARATION METHOD THEREOF

TECHNICAL FIELD

The present invention relates to a combination product comprising phentermine and topiramate as well as the preparation method thereof, especially relates to a combination product comprising phentermine and a sustained-release pellet of topiramate, and as well as the preparation method thereof.

BACKGROUND ART

Obesity refers to excess accumulation and/or abnormal distribution of fat in body, body mass addition, and is a multifactorial chronic metabolic disease, and incidence of obesity increases year by year due to genetic factors, reduction of physical activity and so on. Obesity as a universal internal secretion metabolic disease is not only a worldwide epidemic disease threatening human health, but also closely associated with hyperlipemia, hypertension, diabetes, coronary heart disease and so on (H E Ren, et al., Drug therapy of obesity and advance thereof, Strait Pharmaceutical Journal, 2011, 23(1):88-90). Thus, prevention and treatment of obesity is very important. At present, measures for prevention and treatment of obesity mainly include dietary therapy, sports therapy, drug therapy and surgery etc. For patients with mild obesity, diet control and sports are effective; but for patients with moderate or more serious obesity, weight loss is a long process, dietary and sports therapy alone usually could not solve the problem, and drug therapy is necessary in such situations.

At present, drug for prevention and treatment of obesity are mainly appetite suppressants, especially center appetite suppressants, such as amphetamine, amfepramone, synephrine, fenfluramine, sibutramine as well as fluoxetine among antidepressants, and lipase inhibitor orlistat (trade name: Xenical), etc. However, the above drugs all have adverse reaction or toxic and side effects in different extents, such as cardiovascular system dysfunction, cardiac valves dysfunction, arrhythmia, pulmonary hypertension, respiratory system dysfunction, etc.

Phentermine (2-methyl-1-phenylpropan-2-amine) (Formula 1) is the most popular appetite suppressant developed for obese people in the US, has been approved as short-term auxiliary anti-obesity agent by FDA for a long time, and can be used in combination with exercise, change of living habit and reduction of caloric intake to achieve effects of weight loss in patients. It is a short-term neurotransmitter regulator, can help people having serious problem of body weight to correct dietary behavior, and achieve the goal of permanently remolding body figure by changing dietary habit. At present, its dosage forms used in clinic are: 8 mg tablets, 15 mg and 30 mg tablets and capsules, 18.75 mg and 37.5 mg tablets and capsules, 15 mg and 30 mg orally disintegrating tablets, and 15 mg and 30 mg sustained-release capsules. The therapeutic effects of phentermine depend on many factors such as dose, age of patients, gender, physiological and mental conditions. However, long-term use of phentermine may have risks of addiction and other adverse symptoms (increase in heart rate and blood pressure).

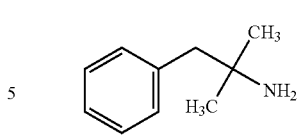

Formula 1

Topiramate (2,3,4,5-bis-O-(1-methylethylidene)-β-D-fructopyranose sulfamate) (Formula 2) is a broad spectrum nerve therapeutic agent approved by FDA in 1995, and has been used in clinic for many years for treatment of some epileptic seizures and prevention of migraine headache (E. Faught, et al., (1996) Neurology 46:1684-1690), and many documents disclosed the good therapeutic effects of topiramate in treatment of diabetes (U.S. Pat. No. 7,109,174B2 and U.S. Pat. No. 6,362,220B1), dysneuria (U.S. Pat. No. 6,908,902B2), depression (U.S. Pat. No. 6,627,653B2), mental disorders (U.S. Pat. No. 6,620,819B2), headache (U.S. Pat. No. 6,319,903B1) and hypertension (U.S. Pat. No. 6,201,010B1).

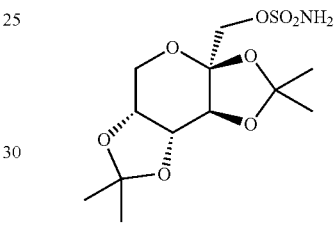

Formula 2

Topiramate is white crystalline powder, has a bitter taste, is freely soluble in organic solvents such as acetone, chloroform, dimethylsulfoxide and ethanol, very freely soluble in alkaline solution having pH of 9-10 such as sodium hydroxide or sodium phosphate solutions, very slightly soluble in water (room temperature) with solubility of only about 9.8 mg/m, and the pH of its saturated solution is 6.3 (Physician's Desk Reference, 56.sup.th ed., pp. 2590-2595 (2002)). Topiramate has linear pharmacokinetic features, can be rapidly and completely absorbed in vivo. After being orally taken in dose of 400 mg by healthy volunteers, it can reach an average plasma peak concentration (Cmax) within 2 h. Plasma concentration of topiramate shows linear relations with dosage in daily dose range from 100 mg to 800 mg, and has a low clearance for oral administration (22-36 ml/min) and a long plasma half-life (19-25 h). Within plasma concentration range of 0.5-250 μm/ml, topiramate has a human plasma protein binding ratio of 15-41%, which decreases with the increase of plasma concentration.

It was found recently that low dose of topiramate and low dose of phentermine in combination is effective in treatment of obesity with less adverse reactions. The main observation indexes of this compound preparation (3.75 mg phentermine/23 mg topiramate) comes up to expectations in both two phase III clinic tests named as EQU IP and CONQUER separately, in comparison with placebo, it could significantly reduce body weight in patients, and more important, the compound preparation showed good safety, it was not observed that this drug could result in QT extension or had any effects on cognition and psychological functions. There was not teratogenic case in the test, the adverse reactions were merely dry mouth and numbed fingers and toes, and these adverse reactions could be alleviated by drinking more water (Progress in Pharmaceutical Sciences, 2009, 33(12): 576-577).

Topiramate has a narrow therapeutic window, because the fluctuation of plasma concentration usually results in some adverse reactions, which are symptoms mainly associated with central nervous system, such as ataxia, attention impairment, confusion, dizziness, fatigue, paresthesia, somnolence, and thinking abnormal, etc. (Physician's Desk Reference, 60th ed., pp 2538-2447(2006)). Thus, in order to improve patient compliance and effect, it is necessary to provide a once-daily dose of sustained-release preparation of topiramate in the composition of phentermine and topiramate.

CN102112126A discloses a composition comprising low-dose rapid-release phentermine and low-dose sustained-release composition of topiramate, a unit dose of the composition comprising 3.75 mg of phentermine and 23 mg of topiramate, in which, the sustained-release composition of topiramate is produced firstly by preparing topiramate drug-loaded matrix cores with 40% w/w of topiramate and 56.5% w/w of microcrystalline cellulose (AvicelPH102) via extrusion-spheronization method using 3.5% w/w of methyl cellulose (Methocel A15LV, MC) as a binding agent, then subjecting to sustained-release coating, and finally forming topiramate pellets with controlled-release function. However, the extrusion-spheronization method is very complicated, both extrusion-spheronization apparatus and coating apparatus are required to fulfill preparation of sustained-release pellet, so that the production process cycle is relatively long, semi-product should be transferred from one apparatus to another, and the use of two manner, i.e., framework and coating, to control the release rate of drug could result in more uncertainty in drug release features.

Thus, it is still in need of providing a combination product comprising phentermine and sustained-release topiramate with simple preparation method, desired drug release, high stability and good drug-release consistency.

Contents of the Invention

With immense amounts of inventive research, the present invention provides a combination product comprising phentermine and sustained-release topiramate, and in comparison with the prior art, this sustained-release pellet of topiramate is free of binding agent in drug layer, and has advantages such as excellent sustained-release effect, simple formulation, easy operation, stable quality, good controllability, and good repeatability. Specifically, the present invention relates to the following aspects.

One aspect of the present invention provides a combination product, which comprises phentermine or salt thereof, and sustained-release pellet of topiramate, in which the sustained-release pellet of topiramate comprises a blank pellet core, a drug layer and a sustained-release coating layer, which is characterized in that the drug layer is free of binding agent.

The drug layer comprises topiramate, and is located on surface of the blank pellet core, and the sustained-release coating layer covers external surface of the drug layer (which structure can be seen in, for example, FIG. 4).

In the combination product according to the present invention, the binding agent can be any binding agents known in the art, including but not being limited to starch slurry, syrup, polyvinylpyrrolidone (povidone, PVP, such as PVP K30), methyl cellulose (MC), ethyl cellulose (EC), highly-substituted hydroxypropyl cellulose (H-HPC), hydroxypropyl methyl cellulose (HPMC), sodium carboxymethyl cellulose, gelatin, Arabic gum, and mixtures thereof. When a blank pellet core is loaded with drug without using a binding agent, the time for loading drug is short, and the adhesion degree of pellets is low. In addition, the stability of topiramate drug is significantly improved because the direct contact between topiramate and binding agent is avoided.

In the combination product according to the present invention, the sustained-release coating layer comprises a sustained-release material and other pharmaceutically acceptable excipients, and the sustained-release material can be any sustained-release materials known in the art, including but not being limited to ethyl cellulose, Eudragit NE 30D, Eudragit RS 30D, Eudragit RL30D, and mixtures thereof.

In the combination product according to the present invention, the sustained-release coating layer can further comprises one or more of a plasticizer, a pore former, an anti-adherent, a coloring agent, a light-screening agent, a flavoring, a sweetening agent, etc., in which the plasticizer includes but is not limited to glycerol, propylene glycol, polyethylene glycol, glycerol triacetate, triethyl citrate, phthalates or dibutyl sebacate or a mixture thereof, preferably glycerol triacetate; the pore former includes but is not limited to polyethylene glycols, povidone, sucrose, salts, hydroxypropyl methyl cellulose, hydroxypropyl methyl cellulose or a mixture thereof, preferably povidone (PVP K30); the anti-adherents includes but is not limited to talc powder, magnesium stearate, aerosil or a mixture thereof, preferably talc powder; the light-screening agent includes but is not limited to titanium dioxide, etc.; the coloring agent includes but is not limited to iron oxide yellow, iron oxide red, carmine, lemon yellow, sunset yellow, indigo blue, etc.; the flavoring agent includes but is not limited to mint essence, lemon essence, orange essence, eucalyptol, syringyl alcohol, etc.; and the sweetening agent includes but is not limited to aspartame, vanillin, sorbitol, mannitol, artificial essences, or a mixture thereof.

In one embodiment of the present invention, the sustained-release coating layer comprises ethyl cellulose and PVP K30.

With lots of experiments, the inventors found that when the sustained-release coating layer comprising ethyl cellulose and PVPK30 in combination is used, the above topiramate drug-loaded pellet has unexpected good effects as compared to coating layers with other sustained-release materials. That is, the topiramate pellet prepared with ethyl cellulose and PVP K30 as sustained-release coating layer material has better stability in drug release, which ensures consistency of drug release in different batches of samples, and the expected sustained-release effects can be achieved without heat treatment after coating. Thus, the coating process is simplified, and the influence of heat treatment after coating on drug release is avoided as well.

Preferably, the weight ratio of ethyl cellulose to PVP K30 is (1:0.20)-(1:0.45), for example (1:0.25)-(1:0.40), for example (1:0.30)-(1:0.35).

In the combination product according to the present invention, the range of weight gain from sustained-release coating (weight percentage of sustained-release material to coating matrix, w/w) can be determined by tests, and generally, the range of weight gain from sustained-release coating is 2%-30%, for example 3%-20%, for example 5%-15%, for example 5%-10%, for example 5%-8%, for example 6%-8%.

In the combination product according to the present invention, the drug layer of sustained-release pellet of topiramate comprises topiramate, and can further comprise other pharmaceutically acceptable excipient(s), such as surfactant(s), disintegrating agent(s), flavoring agent(s), sweetening agent(s), anti-adherent(s), light-screening agent(s), etc. The surfactants include anionic surfactants, cationic surfactant, zwitterionic surfactants, and non-ionic surfactants, including but not being limited to sodium dodecyl sulfate, sodium hexadecanol sulfate, sodium octadecanol sulfate, sodium dodecyl benzene sulfate, dioctyl sodium sulfosuccinate, dihexyl sodium sulfosuccinate, lecithin, sorbitan fatty acid esters, polyoxyethylene sorbitan fatty acid esters, polyoxyethylene fatty acid esters, polyoxyethylene fatty alcohol ethers, polymer of ethylene oxide and propylene oxide, polyoxyethylene 40 monostearate, polyoxyethylene 50 stearate, oxirane triblock copolymer, epoxypropane triblock copolymer, sorbitan monopalmitate (Span-40), sorbitan monostearate (Span-60), glyceryl monostearate, polyoxyethylene stearate, or mixtures thereof; the disintegrating agents include but are not limited to microcrystalline cellulose, low-substituted hydroxypropyl cellulose sodium, crosslinked polyvinylpyrrolidone, sodium carboxymethyl starch, pre-gelatinized starch, alginic acid, starch, effervescing disintegrants, or mixtures thereof; the anti-adherents include but are not limited to talc powder, magnesium stearate, aerosil, preferably talc powder; the light-screening agents include but are not limited to titanium dioxide, etc.; the flavoring include but are not limited to mint essence, lemon essence, orange essence, eucalyptol, syringly alcohol, etc.; the sweetening agents include but are not limited to aspartame, vanillin, sorbitol, mannitol, artificial essences, etc.

In one embodiment of the present invention, the drug layer of sustained-release pellet of topiramate consists of topiramate.

In the present invention, the blank pellet cores refer to pellet cores without physiological activity, and may include but not be limited to sugar pellets, microcrystalline cellulose pellets, starch pellets, or silicon dioxide pellets, etc. In one embodiment of the present invention, the blank pellet cores are sugar pellets. The blank pellet core has particle size of 150 μm-1500 μm, for example 250-1000 μm, for example 300-900 μm, for example 400-850 μm, for example 610-750 μm. The blank pellet cores can be purchased, or prepared by conventional means such as extrusion spheronization method, or fluidized bed method.

In the combination product according to the present invention, in the sustained-release pellet of topiramate, topiramate as active ingredient is in an amount of 10%-50%, preferably 15%-45%, more preferably 20%-40%, relative to the total weight of the combined product. In unit preparation, the active ingredient is in an amount of 0.1 mg-500 mg, preferably 1 mg-300 mg, more preferably 10 mg-250 mg, most preferably 10 mg-50 mg, and optimally 23 mg.

In a preferable embodiment of the present invention, the drug layer of sustained-release pellet of topiramate comprises topiramate, the sustained-release coating layer uses ethyl cellulose as sustained-release coating material, PVP K30 as pore former, and the usage amount ratio of ethyl cellulose to PVP K30 is 1:0.20-1:0.45.

In another preferable embodiment of the present invention, the drug layer of sustained-release pellet of topiramate comprises topiramate, the sustained-release coating layer uses ethyl cellulose as sustained-release coating material, PVP K30 as pore former, the usage amount ratio of ethyl cellulose to PVP K30 is 1:0.20-1:0.45, and the range of weight gain from the sustained-release coating is 5%-15%.

In another preferable embodiment of the present invention, the blank pellet cores are sugar pellets, the drug layer of sustained-release pellet of topiramate comprises topiramate, in the sustained-release coating layer, ethyl cellulose is sustained-release coating material, PVP K30 is pore former, the usage amount ratio of ethyl cellulose to PVP K30 is 1:0.20-1:0.45, and the range of weight gain from the sustained-release coating is 5%-15%.

In further another preferable embodiment of the present invention, the blank pellet cores are sugar pellets with particle size of 610 μm-750 μm, the drug layer of sustained-release pellet of topiramate comprises topiramate, in the sustained-release coating layer, ethyl cellulose is sustained-release coating material, PVP K30 is pore former, the usage amount ratio of ethyl cellulose to PVP K30 is 1:0.25-1:0.4, the range of weight gain from the sustained-release coating is 5%-10%.

In further another preferable embodiment of the present invention, the blank pellet cores are sugar pellets with particle size of 610 μm-750 μm, the drug layer of sustained-release pellet of topiramate uses topiramate as active drug, in the sustained-release coating layer, ethyl cellulose is sustained-release coating material, PVP K30 is pore former, the usage amount ratio of ethyl cellulose to PVP K30 is 1:0.25-1:0.4, and the range of weight gain from the sustained-release coating is 5%-8%.

In a special embodiment of the present invention, the blank pellet cores are sugar pellets with particle size of 610 μm-750 μm, the drug layer of sustained-release pellet of topiramate is topiramate, in the sustained-release coating layer, the ethyl cellulose is sustained-release coating material, PVP K30 is pore former, the usage amount ratio of ethyl cellulose to PVP K30 is 1:0.3-1:0.35, and the range of weight gain from the sustained-release coating is 6%-8%.

In the combination product according to the present invention, the sustained-release pellet of topiramate thereof can bring about good therapeutic effect by one administration per 24 h, the in vivo plasma concentration of drug is stable, peak concentration decreases significantly, and good sustained-release effect is fulfilled. The sustained-release pellet of topiramate of the present invention has in vitro release rate of: not greater than 35% within 1 h, between 30% and 60% within 4 h, between 60% and 90% within 8 h, and not less than 90% within 16 h; preferably, not greater than 25% within 1 h, between 35% and 55% within 4 h, between 60% and 85% within 8 h, and not less than 90% within in 16 h; most preferably, not greater than 25% within 1 h, between 35% and 55% within 4 h, between 65% and 85% within 8 h, and not less than 90% within 16 h.

The preferable conditions for determining the release rate in the present invention are in accordance with the first method (for sustained-release preparation or controlled-release preparation) of Release Rate Measurement (Appendix X D) of Part II of Chinese Pharmacopoeia, 2010 Edition, using apparatus as stated in the second method (slurry method) of Dissolution Rate Measurement (Appendix X C) of Part II of Chinese Pharmacopoeia, 2010 Edition, in which samples are taken and analyzed at different specified time points by using water (500 ml) as releasing media, at 37° C. and rotation speed of 100 rpm.

In the combination product according to the present invention, the phentermine or salt thereof is of rapid-release pellet, which can be rapidly released after oral administration.

In the combination product according to the present invention, the salt of phentermine is, for example, hydrochloride, i.e., phentermine hydrochloride.

In the combination product according to the present invention, the immediate-release pellet of phentermine comprises phentermine as active drug, a filling agent and a binding agent, the filling agent includes but is not limited to microcrystalline cellulose, lactose, sucrose, etc.; the binding agent includes but is not limited to starch slurry, syrup, polyvinylpyrrolidone (povidone, PVP, such as PVP K30), methyl cellulose (MC), ethyl cellulose (EC), highly-substituted hydroxypropyl cellulose (H-HPC), hydroxypropyl methyl cellulose (HPMC), sodium carboxymethyl cellulose, gelatin, Arabic gum, sodium alginate, etc. The pellet of phentermine can further comprise other pharmaceutically acceptable excipient(s), such as surfactant(s), disintegrating agent(s), flavoring agent(s), sweetening agent(s), anti-adherent(s), light-screening agent(s), plasticizer(s), etc. The surfactants include anionic surfactants, cationic surfactant, zwitterionic surfactants, and non-ionic surfactants, including but not being limited to sodium dodecyl sulfate, sodium hexadecanol sulfate, sodium octadecanol sulfate, sodium dodecyl benzene sulfate, dioctyl sodium sulfosuccinate, dihexyl sodium sulfosuccinate, lecithin, sorbitan fatty acid esters, polyoxyethylene sorbitan fatty acid esters, polyoxyethylene fatty acid esters, polyoxyethylene fatty alcohol ethers, polymer of ethylene oxide and propylene oxide, polyoxyethylene 40 monostearate, polyoxyethylene 50 stearate, oxirane triblock copolymer, epoxypropane triblock copolymer, sorbitan monopalmitate (Span-40), sorbitan monostearate (Span-60), glyceryl monostearate, polyoxyethylene stearate, or mixtures thereof; the disintegrating agents include but are not limited to microcrystalline cellulose, low-substituted hydroxypropyl cellulose sodium, crosslinked polyvinylpyrrolidone, sodium carboxymethyl starch, pregelatinized starch, alginic acid, starch, effervescing disintegrants, or mixtures thereof; the anti-adherents include but are not limited to talc powder, magnesium stearate, aerosil, preferably talc powder; the light-screening agents include but are not limited to titanium dioxide, etc.; the flavoring agents include but are not limited to mint essence, lemon essence, orange essence, eucalyptol, syringly alcohol, etc.; the sweetening agents include but are not limited to aspartame, vanillin, sorbitol, mannitol, artificial essences, etc.; the sweetening agent includes but is not limited to aspartame, vanillin, sorbitol, mannitol, artificial essences, etc.; the plasticizer includes but is not limited to glycerol, propylene glycol, polyethylene glycol, glycerol triacetate, triethyl citrate, phthalates and dibutyl sebacate, etc.

In the combination product according to the present invention, the phentermine as active ingredient in the immediate-release pellet of phentermine, is in an amount of 1%-30%, preferably 2%-20%, more preferably 3%-15%, relative to the total weight of phentermine pellet. Unit preparation can have active ingredient in an amount of 1 mg-40 mg, preferably 2 mg-35 mg, more preferably 3 mg-30 mg, most preferably 3.5 mg-20 mg, optimally 3.75 mg-15 mg. The amount or dose of phentermine refers to amount or dose of phentermine per se, and when salt of phentermine is used, conversion should be performed, for example, when the dose of phentermine is 3.75 mg, which corresponds to 4.92 mg of phentermine hydrochloride.

In the combination product according to the present invention, the immediate-release pellet of phentermine has a dissolution rate of at least 80% or more of labeled content dissolved within 30 min; preferably, the dissolution rate is at least 80% or more of labeled content dissolved within 15 min; and most preferably, the dissolution rate is at least 80% or more of labeled content dissolved within 5 min.

The immediate-release pellet of phentermine as prepared in the present invention has a particle size of 150 μm-1500 μm, preferably 300 μm-1000 μm, more preferably 400 μm-850 μm, most preferably 610 μm-750 μm.

The pellet of phentermine and the pellet of topiramate in the present invention can be further processed to form various suitable preparations, for example, can be loaded in capsules to form phentermine-topiramate capsules, or be tableted to form tablets.

The combination product according to the present invention is capsule or tablet. In one embodiment of the present invention, the combination product is capsule.

In the combination product according to the present invention, the content of topiramate in unit preparation can be 1 mg-500 mg, the content of phentermine can be 1 mg-40 mg; preferably, the content of topiramate is 5 mg-300 mg, the content of phentermine is 2 mg-35 mg; more preferably, the content of topiramate is 10 mg-250 mg, the content of phentermine is 3 mg-30 mg; most preferably, the content of topiramate is 20 mg-100 mg, the content of phentermine is 3.5 mg-20 mg; optimally, the content of topiramate is 23 mg-92 mg, the content of phentermine is 3.75 mg-15 mg.

In one embodiment of the present invention, unit preparation comprises 23 mg of topiramate, and 3.75 mg of phentermine; in another embodiment of the present invention, unit preparation comprises 46 mg of topiramate, and 7.5 mg of phentermine; in further another embodiment of the present invention, unit preparation comprises 92 mg of topiramate, and 15 mg of phentermine.

Another aspect of the present invention relates to a method for preparing a sustained-release pellet of topiramate in the combination product according to the invention, the method comprising the following procedure:

a) dissolving ingredients of the drug layer with suitable amount of solvent, and coating a blank pellet core with the obtained drug solution to give a drug-loaded pellet;

b) coating the drug-loaded pellet obtained in step a) with ingredients of sustained-release coating layer.

In the preparation method according to the present invention, the step b) comprises the following steps:

dissolving ingredients of the sustained-release coating layer in a solvent, and coating the drug-loaded pellet obtained in step a) with the resultant solution.

In an embodiment of the present invention, the method for preparing a sustained-release pellet of topiramate comprises the following steps:

a) dissolving the topiramate and optional other excipients of drug layer with suitable amount of solvent under the condition of heating and stirring, placing blank pellet core in a fluidized bed coating pan for marumerization, and coating the blank pellet core with the obtained solution under stirring to give drug-loaded pellet.

b) dissolving a sustained-release coating material and optional other excipients of sustained-release coating layer in a solvent under the condition of heating and stirring, mixing homogeneously, passing through a 100-mesh sieve, to obtain a sustained-release coating solution;

c) spraying the surface of the drug-loaded pellet with the sustained-release coating solution in a fluidized bed to give a sustained-release pellet of topiramate.

In the preparation method according to the present invention, the solvent is water, ethanol, acetone, propylene glycol, chloroform or a mixture thereof, for example, the solvent is a mixture of water and ethanol, for example, can be 50% ethanol water solution, 70% ethanol water solution, 95% ethanol water solution.

In one specific embodiment of the present invention, the method for preparing topiramate pellet comprises:

a) Topiramate is provided as main drug, dissolved with ethanol solution to prepare a drug-loading and coating solution with concentration of 15-25% (w/v), preferably 20% (w/v). A blank pellet core is placed in a fluidized bed coating pan for one step pelletization, and the above drug-loading and coating solution is used for drug loading and coating under stirring to obtain a drug-loaded pellet core.

b) Ethyl cellulose as sustained-release coating material is dissolved in ethanol solution to achieve a concentration of 3-8% (w/v), preferably 5-7% (w/v), and added with a suitable amount of specific pore former, PVP K30, then dissolved under the condition of heating and stirring, stirred homogenously, after passing through 100-mesh sieve, the obtained solution is atomized and sprayed on the drug-loaded pellet core with active drug layer of topiramate in a fluidized bed bottom-spraying coating pan to conduct sustained-release coating.

The process parameters for drug-loading and coating and sustained-release coating in the fluidized bed can be regulated according to practical situations, and preferable process parameters are as follows:

Drug-loading and coating—inlet air temperature is 50-70° C. (to keep pan internal temperature at 40±2° C.); inlet air pressure is 0.3-0.5 bar; atomization pressure is 1.0-2.0 bar; solution spray rate is 5-15 g/min.

Sustained-release coating—inlet air temperature is 40-45° C. (to keep pan internal temperature at 30-35° C.); inlet air pressure is 0.3-0.5 bar; atomization pressure is 1.0-2.0 bar; solution spray rate is 3-12 g/min.

In the present invention, the pellet of phentermine can be prepared by conventional methods for preparation of pellet, such as centrifugation pelletization, extrusion spheronization, and fluidized bed drug-loading and coating method.

Specifically, the following method can be used for the preparation: 400 g of blank sucrose pellet cores is placed in a centrifugation pelletizer, phentermine or salt thereof is weighed, added to a feeder of the pelletizer, and homogeneously laminated on the cores by spraying with binding agent and other excipients, thereafter, the obtained product are taken out, dried to obtain immediate-release drug-loaded pellets of phentermine. The following method can also be used for the preparation: phentermine or salt thereof is weighed, homogeneously mixed with a filling agent and other excipients, added with a binding agent to obtain a suitable soft material, the soft material is placed in a spheronizator, extruded and spheronized, and the obtained pellets are dried, sieved, to obtain rapid-release pellets of phentermine. The following method can also be used for the preparation: phentermine or salt thereof and a suitable amount of binding agent and other excipients are weighed, and dissolved with a suitable solvent to obtain a drug-containing coating solution. Blank pellet cores are weighed, placed in a fluidized bed bottom spray coating pan, and the drug-containing coating solution is sprayed in manner of bottom spray to the surface of the blank pellet cores when the blank pellet cores are in fluidized state. The materials are further fluidized for 5 min after drug-loading, then taken out to obtain immediate-release drug-loaded pellets of phentermine.

The present invention further relates to a use of the combination product of the present invention in manufacture of a medicament for reducing body weight, reducing blood fat, lowering blood pressure, and treatment of metal or nervous diseases.

The present invention further relates to a use of the combination product of the present invention in manufacture of a medicament for treatment of hyperlipidemia, hypertension, diabetes, or coronary heart disease.

The present invention further relates to a method for realizing weight loss, blood fat reduction, antihypertension and treatment of mental or nervous diseases in a subject, comprising administering the subject in such need a therapeutically effective amount of the combination product of the present invention.

In the present invention, the unit preparation refers to a physically dispersed unit, which is suitably used as unit dose for treatment of individual. That is, the composition is formulated as dispersive dose units, each contains active agent in amount of predetermined "unit dose", and the amount is calculated so as to bring about expected therapeutic effects together with the required pharmaceutically acceptable carrier.

In the present invention, the sustained-release pellet can also be called as controlled-release pellet or sustained-release/controlled-release microsphere.

In the present invention, the term "combination product" refers to a product in which phentermine or salt thereof and topiramate are used in combination. The combination product can be a pharmaceutical composition comprising of phentermine or salt thereof and topiramate as two active ingredients, or two pharmaceutical compositions which are prepared with phentermine or salt thereof and topiramate, respectively. Preferably, the two separate pharmaceutical compositions are: a immediate-release preparation comprising phentermine or salt thereof, preferably immediate-release pellet; and a sustained-release or controlled-release preparation comprising topiramate, preferably sustained-release pellet. In the combination product, the phentermine or salt thereof and topiramate can be simultaneously or separately administered to the individual in need of such treatment; or phentermine or salt thereof is administered first, then topiramate is administered after an interval of time; or topiramate is administered first, then phentermine or salt thereof is administered after an interval of time; the interval of time can be determined according to the pharmacologic or pharmacokinetic features of the two drugs.

SPECIFIC MODELS FOR CARRYING OUT THE INVENTION

Figure 1:
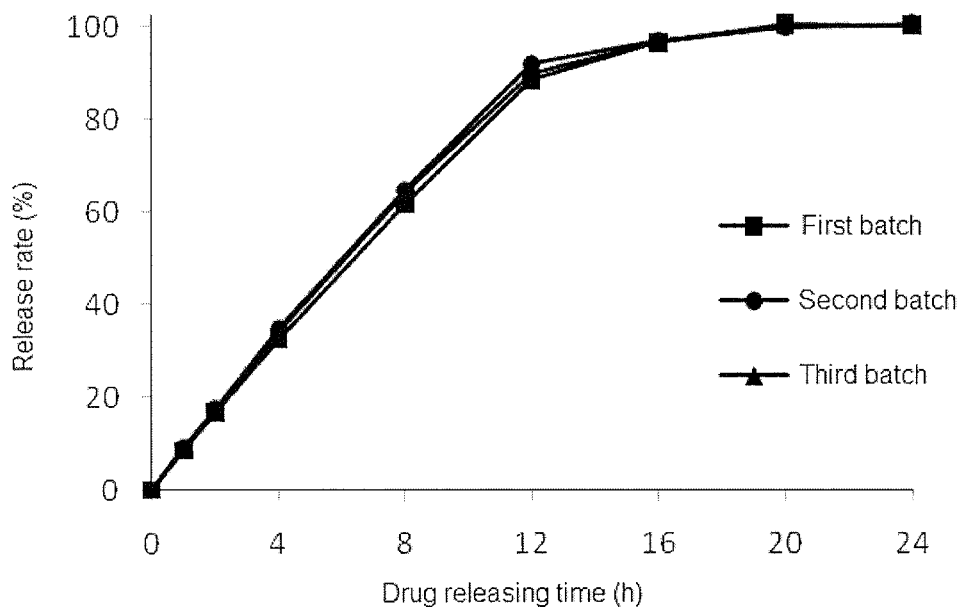
FIG. 1 shows release profiles in water for the 3 batches of sustained-release coating pellets of topiramate of Example 6.

The embodiments of the present invention are further illustrated with the following examples. Those skilled in the art would understand that the following examples are merely used for illustrating the present invention, rather than restricting the scope of the present invention. If specific conditions were not given in the examples, conventional conditions or conditions suggested by manufacturers were used. If manufacturers of the used reagents or instruments were not given, they were all conventional products commercially available in markets.

In the following examples, unless specifically pointed out, the obtained parameters were all calculated according to the following formulations:

Pellet drug-loading rate (%)=($W_{total\ weight\ of\ pellets}$−$W_{blank\ pellet\ core\ weight}$)/$W_{amount\ of\ bulk\ drug}$×100%

Weight gain from sustained-release coating (%)= ($W_{total\ weight\ of\ pellets\ after\ sustained\text{-}release\ coating}$−$W_{total\ weight\ of\ pellets\ before\ sustained\text{-}release\ coating}$)/$W_{total\ weight\ of\ pellets\ after\ sustained\text{-}release\ coating}$×100%

Adhesion rate of pellet= ($W_{total\ weight\ of\ pellets\ after\ coating}$−$W_{total\ weight\ of\ pellets\ without\ adhesion}$)/$W_{total\ weight\ of\ pellets\ after\ coating}$×100%

In the examples of the present invention, unless specifically pointed out, release rates of topiramate were measured by the following method. According to the first method (for sustained-release preparation or controlled-release preparation) of Release Rate Measurement (Appendix X D) of Part II of Chinese Pharmacopoeia, 2010 Edition, the apparatus as stated in the second method (slurry method) of Dissolution Rate Measurement (Appendix X C) of Part II of Chinese Pharmacopoeia, 2010 Edition, was used to perform the measurement using water (500 ml) as releasing media, at 37° C. and rotation speed of 100 rpm. Samples (5 ml, supplemented with equivalent volume of media at the meantime) were taken at specified time points and filtrated, the subsequent filtrates were used as test solutions. High performance liquid chromatography (Appendix V D, Part II, Chinese Pharmacopoeia, 2010 Edition) was used, octylsilane-bonded silica gel was used as packing agent, column temperature was 35° C., 50% methanol was mobile phase, differential refractive detector was used, and the flow rate was 1.5 ml per minute. 200 µl of test solution was taken, injected in liquid chromatograph, the peak area of topiramate as main drug was recorded; topiramate was separately taken as control sample and measured by the same method, and accumulative release percentages of drug at different time points were calculated by external standard method.

EXAMPLE 1

Comparison in Drug-Loading and Coating Between Drug-Containing Solutions with and without Binding Agent Formulation:

| Formulation | Topiramate (g) | Binding agent (g) | | | | 50% ethanol (ml) |
|---|---|---|---|---|---|---|
| | | HPMC | PVP | HPC | Free of binding agent | |
| 1 | 230 | 6.9 g | — | — | — | 1150 |
| 2 | 230 | — | 6.9 g | — | — | 1150 |
| 3 | 230 | — | — | 6.9 g | — | 1150 |
| 4 | 230 | — | — | — | — | 1150 |

Preparation Method:

4 Parts of topiramate raw material were weighed, 230 g per part, separately added with suitable amount of 50% ethanol, stirred under heating at 40° C.-50° C. for dissolution; then HPMC (E5), PVP K30 and HPC, each 6.9 g, were separately weighed, added in order to the first part, the second part, and the third part solutions, while the fourth part was free of binding agent; then the obtained samples were stirred and heated at 40° C.-50° C. for dissolution, and then each part was added with 50% ethanol to reach 1150 ml to obtain drug-containing coating solutions with different binding agents.

500 g of sucrose pellet cores (610-750 µm) were placed in a fluidized bed bottom spray coating pan, and the inlet air temperature was set at 55° C. (to keep pan internal temperature at 40±2° C.); inlet air pressure was 0.35 bar; atomization pressure was 1.5 bar; solution spray rate was 5-15 g/min (regulated according to fluidization state at any time). The drug-containing coating solution was sprayed in manner of bottom spray on surface of sucrose pellet cores when the sucrose pellet cores were in fluidization state, after the end of drug-loading, the material was further fluidized at 45° C. for 5 min to obtain drug-loaded pellets with different binding agents, which were weighed, and results were shown in Table 1.

TABLE 1

Results of drug-loading and coating using drug-containing solutions with and without a binding agent

| Index | Formulation 1 | Formulation 2 | Formulation 3 | Formulation 4 |
|---|---|---|---|---|
| Adhesion degree (%) | 7.8 | 3.7 | 5.5 | 2.1 |
| Drug-loading time (min) | 71 | 62 | 68 | 54 |
| Drug-loading rate of pellet (%) | 94.2 | 93.7 | 95.1 | 95.4 |

EXAMPLE 2

Results of Drug-Loading and Coating Using Drug-Containing Coating Solutions with Different Solvents as Dissolvent 4 Parts of topiramate raw material were weighed, 230 g per part, separately added with suitable amount of 50% ethanol, 70% ethanol, 95% ethanol, and anhydrous ethanol, stirred and heated at 40° C.-50° C. for dissolution; then corresponding solvent was supplemented to reach 1150 ml to obtain drug-containing coating solutions with different solvents as dissolvent.

500 g of sucrose pellet cores (610-750 µm) were placed in a fluidized bed bottom spray coating pan, and the inlet air temperature was set at 55° C. (to keep pan internal temperature at 40±2° C.); inlet air pressure was 0.35 bar; atomization pressure was 1.5 bar; solution spray rate was 5-15 g/min (regulated according to fluidization state at any time). The drug-containing coating solution with different solvents as dissolvent was sprayed on surface of blank sucrose pellet cores in manner of bottom spray when the sucrose pellet cores were in fluidization state, after the end of drug-loading, the material was further fluidized at 45° C. for 5 min to obtain drug-loaded pellets with different solvents as dissolvent, which were weighed, and results were shown in Table 2.

TABLE 2

Drug-loading and coating results of drug-containing coating
solutions with different solvents as dissolvent

| Index | 50% ethanol | 70% ethanol | 95% ethanol | Anhydrous ethanol |
|---|---|---|---|---|
| Adhesion degree (%) | 2.1 | 2.2 | 1.9 | 1.8 |
| Drug-loading time(min) | 54 | 50 | 48 | 44 |
| Drug-loading rate on pellet (%) | 95.4 | 94.5 | 91.6 | 90.4 |

EXAMPLE 3

Comparison of Release Rates of Sustained-Release Pellets of Topiramate with Blank Pellet Cores Having Different Particle Size Formulation
1) Formulation of Drug-Loaded Pellet:

| Formulation | Topiramate (g) | Blank pellet core | |
|---|---|---|---|
| | | Range of particle size (µm) | Weight (g) |
| 5 | 230 | 300-400 | 500 |
| 6 | 230 | 500-610 | 500 |
| 7 | 230 | 610-750 | 500 |

2) Formulation of Sustained-Release Coating Layer:

| Formulation | Ethyl cellulose (g) | PVP K30 (g) |
|---|---|---|
| 5 | 50 | 16.5 |
| 6 | 40 | 13.2 |
| 7 | 30 | 10.0 |

Preparation Method:

(1) 230 g of topiramate was weighed, added with a suitable amount of 50% ethanol, stirred and heated at 40-50° C. for dissolution, and added 50% ethanol to reach 1150 ml to obtain a drug-containing coating solution.

300 µm-400 µm, 500 µm-610 µm, 610 µm-750 µm sucrose pellet cores were separately weighed, each 500 g, placed in a fluidized bed bottom spray coating pan, the inlet air temperature was set at 55° C. (to keep pan internal temperature at 40±2° C.); inlet air pressure was 0.35 bar; atomization pressure was 1.5 bar; solution spray rate was 5-15 g/min (regulated according to fluidization state at any time). The drug-containing coating solution was sprayed in manner of bottom spray on surface of sucrose pellet cores when the sucrose pellet cores were in fluidization state, and after the end of drug-loading, the material was further fluidized at 45° C. for 5 min to obtain drug-loaded pellets of topiramate.

(2) The formulation amount of ethyl cellulose (EC) was weighed, added with suitable amount of 95% ethanol for dissolution, then added with the formulation amount of PVP K30, dissolved, and added with 95% ethanol to suitable amount to obtain a sustained-release coating solution.

(3) The above drug-loaded pellets of topiramate with different particle size were weighed, 500 g each, and separately placed in a fluidized bed bottom spray coating pan, the inlet air temperature was set at 40-45° C. (to keep pan internal temperature at 30-35° C.); inlet air pressure was 0.35 bar; atomization pressure was 1.5 bar; solution spray rate was 3-12 g/min. The sustained-release coating solutions of the above 3 formulations were separately sprayed in manner of bottom spray on surfaces of drug-loaded pellets with different particle size when the drug-loaded pellets were in fluidization state, to obtain sustained-release pellets of topiramate with different particle size, wherein the weight gain from sustained-release coating were 10.9%, 8.8% and 6.7%, respectively. According to calculation, the adhesion degrees of pellets were separately 2.2%, 2.1%, 1.8%, respectively.

The measurement results of drug release rates of the prepared sustained-release pellets of topiramate were shown in Table 3.

TABLE 3

Evaluation results of release rates of pellets with different particle size

| Formulation | particle size of blank pellet cores | Release rate (%) | | | | | |
|---|---|---|---|---|---|---|---|
| | | 1 h | 4 h | 8 h | 12 h | 16 h | 20 h |
| 5 | 300-400 µm | 21.6 | 55.5 | 88.1 | 98.5 | 100.4 | 101.2 |
| 6 | 500-610 µm | 16.7 | 49.5 | 80.6 | 92.4 | 98.5 | 99.6 |
| 7 | 610-750 µm | 19.4 | 56.8 | 85.4 | 96.2 | 99.8 | 100.4 |

EXAMPLE 4

Preparation of Sustained-Release Pellets of Topiramate with Eudragit Sustained-Release Materials Formulation of Sustained-Release Coating:

| | Formulation | | |
|---|---|---|---|
| | 8 | 9 | 10 |
| Drug-loaded pellets | 500 g | 500 g | 500 g |
| Eudragit RS30D | 133 g (corresponding to 40 g of dry resin) | — | — |
| Eudragit NE30D | — | 167 g (corresponding to 50 g of dry resin) | — |
| Eudragit RL30D | — | — | 200 g (corresponding to 60 g of dry resin) |
| Talc powder | 20 | 25 | 30 |
| Water | 246 | 309 | 370 |

Preparation Method:

Aqueous dispersions of Eudragit RS30D, Eudragit NE 30D, Eudragit RL30D in formulation amounts were separately weighed, added with water in equal amount, stirred homogeneously; the talc powder in formulation amount was added to the residual water, homogenized with a high-shear homogenizer for 3 min, the obtained suspension was slowly poured into the above aqueous dispersions, stirred homogeneously, passed through 80 mesh sieve, to obtain sustained-release coating solutions.

500 g of drug-loaded pellets prepared according to Formulation 4 of Example 1 was placed in a fluidized bed bottom spray coating pan, the inlet air temperature was set at 25-30° C. (to keep pan internal temperature at 23-25° C.); inlet air pressure was 0.35 bar; atomization pressure was 1.5 bar; solution spray rate was 3-5 g/min. The above 3 sustained-release coating solutions were separately sprayed on surface of the drug-loaded pellets in manner of bottom spray when the drug-loaded pellets were in fluidization state to obtain 3 kinds of sustained-release pellets of topiramate respectively with Eudragit RS30D, Eudragit NE 30D, and Eudragit RL30D as sustained-release coating material, and the weight gain from sustained-release coating were respectively 9.7%, 11.9%, and 13.9%. The obtained sustained-release pellets of topiramate were subjected to aging and heating treatment in a high temperature oven at 40° C. for 24 h. According to calculation, the adhesion degrees of pellets were 2.8%, 2.7%, 3.0%, respectively.

The measurement results of drug release rates were shown in Table 4.

TABLE 4

Evaluation results of release rates of sustained-release pellets of topiramate with different sustained-release coating materials

| Formulation | Release rate (%) | | | | | |
|---|---|---|---|---|---|---|
| | 1 h | 4 h | 8 h | 12 h | 16 h | 20 h |
| 8 | 19.6 | 44.6 | 70.2 | 88.3 | 97.7 | 99.7 |
| 9 | 15.5 | 34.4 | 66.3 | 77.9 | 92.2 | 94.8 |
| 10 | 16.4 | 36.5 | 68.3 | 79.4 | 95.1 | 98.5 |

EXAMPLE 5

Preparation of Sustained-Release Pellets of Topiramate

Formulation of Sustained-Release Coating

| | Formulation | | |
|---|---|---|---|
| | 11 | 12 | 13 |
| EC | 30 g | 30 g | 30 g |
| PVP K30 | 9 g | 9.6 g | 10.5 g |

Preparation Method:

According to the amount proportions of the above formulations, ethyl cellulose was dissolved with suitable amount of 95% ethanol, then separately added with proportion amounts of PVP K30 and dissolved to obtain sustained-release coating solutions.

500 g of drug-loaded pellets prepared with the drug-containing coating solution without a binding agent of Example 1 was placed in a fluidized bed bottom spray coating pan, the inlet air temperature was set at 40-45° C. (to keep pan internal temperature at 30-35° C.); inlet air pressure was 0.35 bar; atomization pressure was 1.5 bar; solution spray rate was 3-12 g/min. The sustained-release coating solutions with different proportions of ethyl cellulose and PVP K30 were separately sprayed on surface of the drug-loaded pellets in manner of bottom spray when the drug-loaded pellets were in fluidization state, and the weight gain from sustained-release coating were separately 6.56%, 6.65%, and 6.79%, so as to obtain sustained-release pellets of topiramate with different proportions of ethyl cellulose and PVP K30. According to calculation, the adhesion degrees of pellets were 2.3%, 2.4% and 2.1%, respectively. The measurement results of drug release rate were shown in Table 5

TABLE 5

Evaluation results of release rates of sustained-release pellet of topiramate prepared according to the formulation 11-13

| Formulation | Release rate (%) | | | | | |
|---|---|---|---|---|---|---|
| | 1 h | 4 h | 8 h | 12 h | 16 h | 20 h |
| 11 | 17.4 | 36.6 | 64.3 | 82.5 | 90.7 | 95.5 |
| 12 | 21.8 | 47.6 | 76.4 | 91.3 | 95.7 | 97.8 |
| 13 | 24.2 | 51.4 | 83.8 | 99.7 | 99.6 | 100.2 |

EXAMPLE 6

Experiment of Process Repeatability (1) Preparation of Drug-Loaded Pellet Cores of Topiramate without Binding Agent 276 g of topiramate raw material was weighed, added with suitable amount of 70% ethanol, stirred under heating at 40-50° C., dissolved, added with 70% ethanol to reach 1380 ml, to obtain drug-containing coating solution.

600 g of 610 μm-750 μm sucrose pellet cores was weighed and placed in a fluidized bed bottom spray coating pan, the inlet air temperature was set at 55° C. (to keep pan internal temperature at 40±2° C.); inlet air pressure was 0.35 bar; atomization pressure was 1.5 bar; solution spray rate was 5-15 g/min (regulated according to fluidization state at any time). The drug-containing coating solution was sprayed on surface of blank sucrose pellet cores in manner of bottom spray when the sucrose pellet cores were in fluidization state. After the end of drug-loading, the material was further fluidized at 45° C. for 5 min to obtain topiramate drug-loaded pellet cores without binding agent, which were weighed, the total weight $W_{total}$ of the pellets after the end of drug-loading was recorded, and the drug-loading rate and product yield of the pellets were calculated and shown in Table 6.

TABLE 6

Results of process repeatability of topiramate drug-loaded pellet cores without binding agent

| Sample batch | Production scale (preparation unit/batch) | Amount of the charged main drug (g/batch) | Amount of sucrose pellet cores (g/batch) | output of the drug-loaded pellet cores (g/batch) | Drug-loading rate (%) | Product yield (%) |
|---|---|---|---|---|---|---|
| 1 | 12000 | 276 | 600 | 864 | 95.7 | 98.6 |
| 2 | 12000 | 276 | 600 | 862 | 94.9 | 98.4 |
| 3 | 12000 | 276 | 600 | 863 | 95.3 | 98.5 |

Note:
the dose of topiramate of each preparation unit was expressed as 23 mg;
the product yield was calculated by dividing the amount of drug-loaded pellet cores by the total amount of the charged raw materials and excipients.

(2) Preparation of Sustained-Release Coating Pellet of Topiramate 48 g of Ethyl cellulose was weighed, added with suitable amount of 95% ethanol, stirred under heating at 40° C.-50° C., dissolved, then added with about 16.2 g of PVP K30, stirred under heating at 40° C.-50° C., dissolved, stirred homogenously, added with 95% ethanol to reach 1152 ml, to obtain a sustained-release coating solution.

800 g of drug-loaded pellets as above prepared was placed in a fluidized bed bottom spray coating pan, the inlet air temperature was set at 40-45° C. (to keep pan internal temperature at 30-35° C.); inlet air pressure was 0.35 bar; atomization pressure was 1.5 bar; solution spray rate was 3-12 g/min. The sustained-release coating solution was sprayed on surface of the drug-loaded pellets in manner of bottom spray when the drug-loaded pellets were in fluidization state, to obtain 3 batches of sustained-release pellets of topiramate, and their weight gain from sustained-release coating were separately 6.87%, 6.98%, and 7.08%. According to calculation, the adhesion degrees of pellets were 2.1%, 2.0% and 2.1%, respectively. The results were shown in FIG. 1 and Table 7.

TABLE 7

Experimental results of process repeatability of sustained-release coating pellets of topiramate

| Sample batch | Product amount (preparation unit/batch) | Amount of drug-loaded pellet cores, g/batch | Amount of ethyl cellulose, g/batch | Amount of PVP K30, g/batch | Sustained-release pellet of topiramate, g/batch | Product yield (%) | Release rate (%) | | | |
|---|---|---|---|---|---|---|---|---|---|---|
| | | | | | | | 1 h | 4 h | 8 h | 16 h |
| 1 | 10000 | 800 | 48 | 16.2 | 859 | 99.3 | 14.4 | 37.2 | 68.5 | 96.4 |
| 2 | 10000 | 800 | 48 | 16.2 | 860 | 99.5 | 15.1 | 38.6 | 69.5 | 96.8 |
| 3 | 10000 | 800 | 48 | 16.2 | 861 | 99.6 | 15.9 | 39.1 | 68.8 | 96.4 |

EXAMPLE 7

Figure 2:
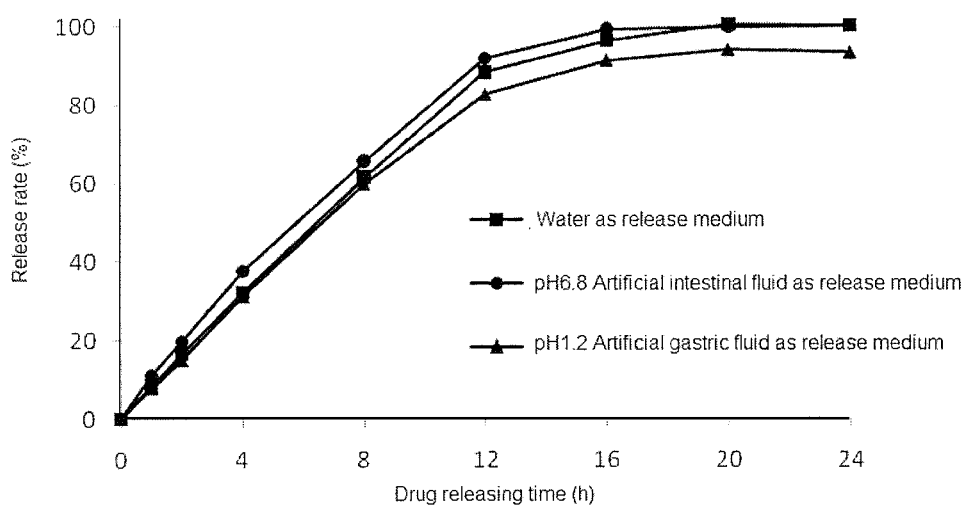
FIG. 2 shows release profiles in different releasing media for the first batch of sustained-release coating pellets of topiramate of Example 6.

Effects of Different Dissolution Media on Release Rate of Sustained-Release Pellet of Topiramate In order to verify whether acidic, basic solvent media would influence the release rate of the sustained-release pellets of the present invention, 0.1 mol/L HCl (pH1.2) was prepared as artificial gastric fluid, 0.2 ml/L phosphate buffer (pH6.8) was prepared as artificial intestinal fluid, and these media and water (500 ml) were used as release media separately, and rotation speed was 100 rpm, 37° C. 5 ml of Samples (supplemented with equivalent volume of media at the meantime) were separately taken at 1, 2, 4, 8, 12, 16, 20, 24 h, filtrated, and the subsequent filtrates were used as test solutions. High performance liquid chromatography (Appendix V D, Part II, Chinese Pharmacopoeia, 2010 Edition) was used, octylsilane-bonded silica gel was used as packing agent, 50% methanol was mobile phase, differential refractive detector was used, and flow rate was 1.5 ml per minute. 200 μl of test solution was taken and injected in liquid chromatography, and the peak area of topiramate as main drug was recorded; moreover, topiramate was taken as reference material and measured by the same method, and accumulative release percentages of drug at different time points were calculated by external standard method. The release profile of sample of Batch 1 in Example 6 (2) in the above mentioned media were drawn, and the results were shown in FIG. 2. The results showed that the drug release profiles of the sustained-release pellet of topiramate in the artificial gastric fluid, water and the artificial intestinal fluid were substantially consistent (since topiramate was unstable in artificial gastric fluid with pH of 1.2 and had degradation reaction, the release rate in the artificial gastric fluid in the present experiment was derived from the sum of main drug, topiramate, and degradation products), which suggested that the product could release drug consistently in different sites of gastrointestinal tract, so as to ensure stable pharmacological effects of topiramate as active ingredient.

EXAMPLE 8

Figure 3:
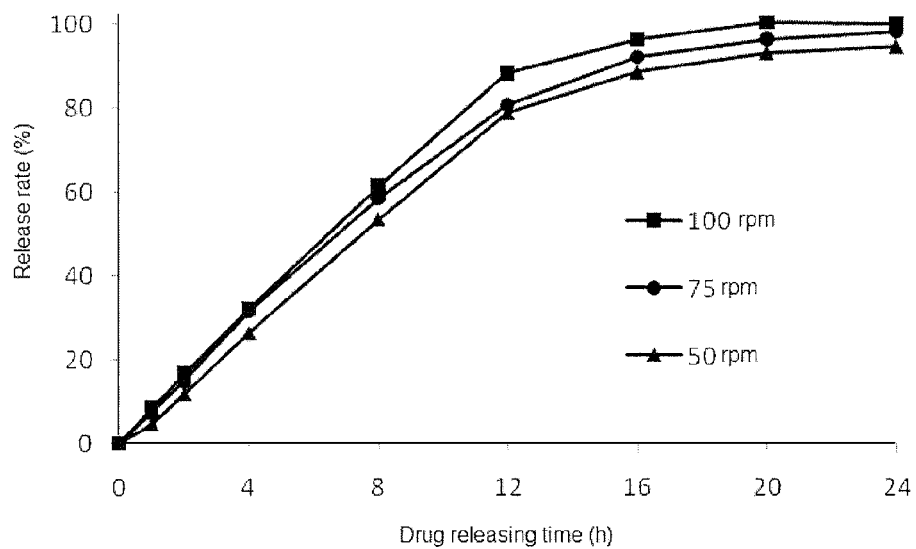
FIG. 3 shows release profiles in conditions of different rotation speeds for the first batch of sustained-release coating pellets of topiramate of Example 6.
Figure 4:
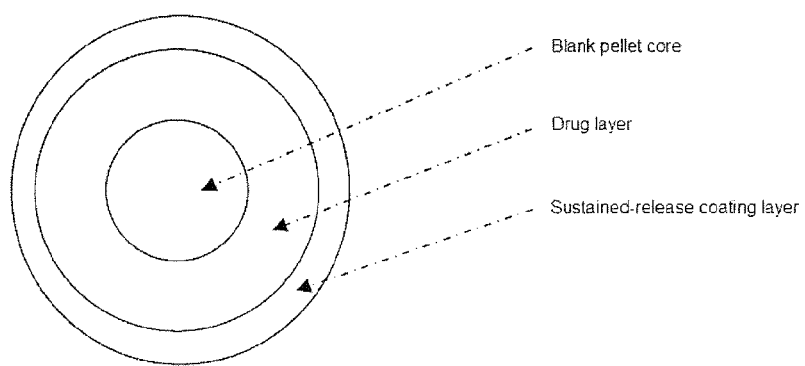
FIG. 4 shows a schematic diagram of structure of the sustained-release pellet of topiramate of the present invention.

Effects of Different Rotation Speeds on Release Rate of Sustained-Release Pellet of Topiramate In order to verify whether gastrointestinal motility would influence the release rate of the sustained-release pellets of the present invention, rotation speed was set at 50 rpm, 75 rpm and 100 rpm, respectively, and water (500 ml) were used as release media, 37° C. 5 ml of sample (supplemented with equivalent volume of media at the meantime) were taken separately at 1, 2, 4, 8, 12, 16, 20, 24 h, filtrated, and the subsequent filtrates were used as test solutions. High performance liquid chromatography (Appendix V D, Part II, Chinese Pharmacopoeia, 2010 Edition) was used, octylsilane-bonded silica gel was used as packing agent, 50% methanol was mobile phase, differential refractive detector was used, and flow rate was 1.5 ml per minute. 200 μl of test solution was taken and injected in liquid chromatography, the peak area of topiramate as main drug was recorded; topiramate was separately taken as reference material and measured by the same method, and accumulative release percentages of drug at different time points were calculated by external standard method. The release profile of sample of Batch 1 in Example 6 (2) under the above mentioned different rotation speeds were drawn, and the results were shown in FIG. 3.

The results showed that the drug release profiles of the sustained-release pellet of topiramate under rotation speed ranging between 50-100 rpm were substantially consistent, which suggested that the product could release drug consistently under different situations of gastrointestinal motility, so as to ensure stable pharmacological effects of topiramate as active ingredient.

EXAMPLE 9

Study on Drug Release Consistency

The preparation of formulation 8-10 was repeated for 3 times according to the method of Example 4, and their drug release consistency was considered. The results were shown in Table 8.

TABLE 8

Results of drug release consistency of sustained-
release pellet of topiramate
(mean ± standard deviation)

| Form-ulation | Drug release rate at different time points (%) (mean ± standard deviation) | | | | |
|---|---|---|---|---|---|
| | 1 h | 4 h | 8 h | 16 h | 20 h |
| Formulation 8 | 19.6 ± 8.7 | 51.2 ± 8.3 | 75.2 ± 9.8 | 93.3 ± 9.1 | 95.7 ± 5.2 |
| Formulation 9 | 15.1 ± 7.1 | 38.8 ± 7.4 | 68.7 ± 8.7 | 92.9 ± 9.8 | 95.3 ± 4.1 |
| Formulation 10 | 14.4 ± 8.8 | 36.5 ± 8.3 | 65.3 ± 9.6 | 92.4 ± 8.1 | 95.1 ± 5.2 |
| Example 6 | 14.4 ± 2.5 | 37.2 ± 1.8 | 68.5 ± 1.4 | 96.4 ± 1.2 | 100.2 ± 0.9 |

EXAMPLE 10

Formulation

Drug Layer

| Formulation | Topiramate (g) | Sodium dodecyl sulfate (g) | Tween 80 (g) | Talc powder (g) |
|---|---|---|---|---|
| 14 | 230 | 3.45 | — | — |
| 15 | 230 | — | 6.90 | — |
| 16 | 230 | — | — | 11.5 |

Sustained Release Layer

| Name | Amount |
|---|---|
| EC (g) | 30 |
| PVP K30 (g) | 10.0 |
| Aerosil (g) | 3.0 |
| 95% ethanol (ml) | 720 |

Preparation Method:

(1) The ingredients of drug layer in the above formulation amounts were weighed, added with suitable amount of 50% ethanol, stirred under heating at 40° C.-50° C., dissolved (formulation 14 and 15) or suspended (formulation 16), and added with 50% ethanol to reach 1150 ml, to obtain drug-containing coating solutions (formulation 14, 15) or suspension (formulation 16).

500 g of 610 μm-750 μm sucrose pellet cores was weighed and placed in a fluidized bed bottom spray coating pan, the inlet air temperature was set at 55° C. (to keep pan internal temperature at 40±2° C.); inlet air pressure was 0.35 bar; atomization pressure was 1.5 bar; solution spray rate was 5-15 g/min (regulated according to fluidization state at any time). The drug-containing coating solutions or suspension were sprayed on surface of blank pellet cores in manner of bottom spray when the sucrose pellet cores were in fluidization state. After the end of drug-loading, the material was further fluidized at 45° C. for 5 min to obtain topiramate drug-loaded pellets.

(2) Ethyl cellulose (EC) in the formulation amount was weighed, added with 95% ethanol, stirred under heating at 40° C.-50° C., dissolved, then added with the formulation amount of PVP K30, stirred under heating at 40° C.-50° C., dissolved, stirred homogeneously, added with the formulation amount of aerosil, added 95% ethanol to the formulation amount, and stirred, to obtain sustained-release coating solution.

The above topiramate drug-loaded pellet cores was separately weighed, each 500 g, and placed in a fluidized bed bottom spray coating pan, the inlet air temperature was set at 40-45° C. (to keep pan internal temperature at 30-35° C.); inlet air pressure was 0.35 bar; atomization pressure was 1.5 bar; solution spray rate was 3-12 g/min. The 3 formulations of the sustained-release coating solutions were sprayed on surface of drug-loaded pellets with different corresponding particle size in manner of bottom spray when the drug-loaded pellets were in fluidization state, to obtain sustained-release pellets of topiramate with different particle size, the weight gain from sustained-release coating were 6.85%, 6.74% and 6.89%, respectively. By calculation the adhesion degrees of pellets were 1.9, 2.0, and 1.7%, respectively. The measurement results of release rates were shown in Table 9.

TABLE 9

Measurement results of drug release rates of formulation 14-16

| Formulation | Release rate (%) | | | | |
|---|---|---|---|---|---|
| | 1 h | 4 h | 8 h | 16 h | 20 h |
| Formulation 14 | 9.60 | 39.6 | 66.3 | 95.7 | 97.1 |
| Formulation 15 | 9.4 | 36.6 | 65.3 | 96.8 | 98.8 |
| Formulation 16 | 9.2 | 37.8 | 68.2 | 96.9 | 99.7 |

EXAMPLE 11

Preparation of Phentermine Pellet

Formulation 17 (Centrifugation Pelletization):

| Phentermine hydrochloride | 74.7 g |
|---|---|
| Blank sucrose pellet cores | 400 g |
| Hydropropyl methyl cellulose | 1.35 g |

Preparation method: 400 g of blank sucrose pellet cores (0.71-0.85 mm) was placed in a centrifugation pelletizer; 74.7 g of phentermine hydrochloride (corresponding to 60 g of phentermine) that had passed through 80-mesh sieve was weighed and added in a feeder of the pelletizer, the rotation speed of main engine was set at 250-330 rpm, air blast flow was 400 L/min, air injection flow was 15-20 L/min, air injection pressure was 0.5-0.6 MPa, 45 ml of 3% (w/v) aqueous solution of hydropropyl methyl cellulose (HPMC) was used as binding agent, solution spray rate was 3-6 ml/min, and rotation speed of powder feeder was 10-20 r/min, so that drug powder was uniformly laminated on mother cores, the material was taken out after the end of powder feeding, and dried at 60° C. for 2 h, to obtain rapid-release pellet of phentermine.

Formulation 18 (Extrusion-Spheronization Method)

| Phentermine hydrochloride | 74.7 g |
|---|---|
| Microcrystalline cellulose | 400 g |
| Hydropropylmethylcellulose | 0.40 g |

Preparation method: 74.7 g of phentermine hydrochloride (corresponding to 60 g of phentermine) that passed through 80-mesh sieve was weighed, homogeneously mixed with 400 g of microcrystalline cellulose, and added with about 13.5 ml of 3% (w/v) aqueous solution of hydropropylmethylcellulose (HPMC) as binding agent to form a suitable soft material. The soft material was placed in a spheronizator, extrusion speed was set at 30 rpm, spheronization speed was 350 rpm, and spheronization time as 5 min, the obtained pellets were dried in 40° C. oven for 4 h, and sieved to obtain 500-800 μm target pellets as immediate-release pellets of phentermine.

Formulation 19 (Fluidized Bed Pellet Core Drug-Loading and Coating Method)

| | |
|---|---|
| Phentermine hydrochloride | 74.7 g |
| Blank sucrose pellet cores | 400 g |
| Hydropropyl methyl cellulose | 6.0 g |

Preparation method: 74.7 g of phentermine hydrochloride (corresponding to 60 g of phentermine) that passed through 80-mesh sieve was weighed, 6.0 g of hydropropylmethylcellulose (HPMC) was weighed as binding agent, they were added with 200 ml of water, stirred and dissolved under heating at 40° C.-50° C., and added with water to reach 300 ml, to obtain a drug-containing coating solution. 400 g of sucrose pellet core (0.71-0.85 mm) was placed in a fluidized bed bottom spray coating pan, inlet air temperature was set at 50-70° C., inlet air pressure was 0.35 bar, atomization pressure was 1.0-2.0 bar, solution spray rate was 3-12 g/min (regulated according to fluidization state at any time). The drug-containing coating solution was sprayed in manner of bottom spray on surface of blank pellet cores when the sucrose pellet cores were in fluidization state, after end of drug-loading, the material was further fluidized at 45° C. for 5 min, and then taken out to obtain drug-loaded pellet of phentermine.

Figure 6:
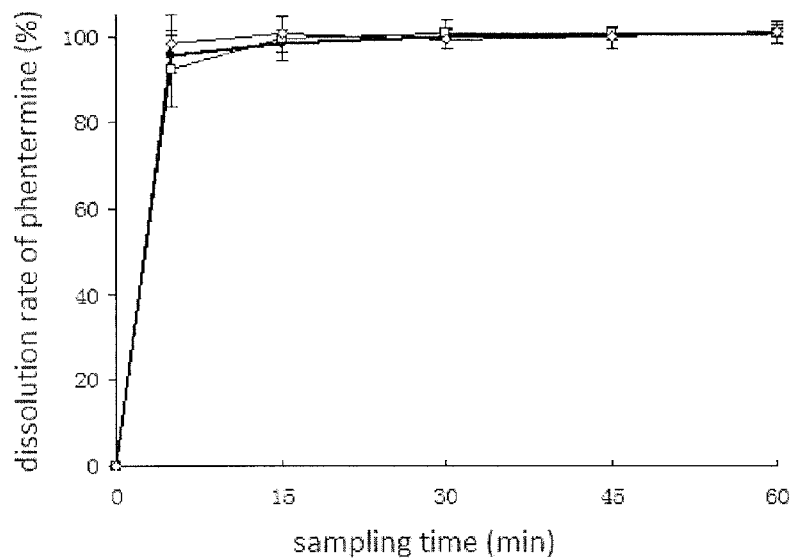
FIG. 6 shows dissolution curves of phentermine pellets.

Measurement of Dissolution Rate of Immediate-Release Pellet of Phentermine:

Appropriate amounts of pellets of phentermine of Formulation 17, Formulation 18 and Formulation 19 (corresponding to 7.5 mg of phentermine) were separately weighed, and measured to determine drug dissolution rates at different time points according to the second method of Dissolution Rate Measurement (Appendix X C, slurry method) of Part II of Chinese Pharmacopoeia, 2010 Edition, using 500 ml of water as releasing media, at 37° C., and rotation speed of 50 rpm. 5 ml of samples supplemented with equivalent volume of media at the meantime) were taken at the time points of 5 min, 15 min, 30 min, 45 min, and 60 min, filtrated, and the subsequent filtrates were used as test solutions. High performance liquid chromatography (Appendix V D, Part II, Chinese Pharmacopoeia, 2010 Edition) was used, octylsilane-bonded silica gel was used as packing agent, column temperature was 35° C., 40% methanol was mobile phase, detection wavelength was 254 nm, and flow rate was 1.5 ml per minute. 20 μl of test solution was taken and injected in liquid chromatograph, and the peak area of phentermine as main drug was recorded; moreover, phentermine was taken as reference sample and measured by the same method, and accumulative dissolution percentages of phentermine as main drug at different time points were calculated by external standard method. The results of dissolution rates of 3 formulations (Formulation 17, Formulation 18 and Formulation 19) were shown in Table 10, and dissolution rate curves were shown in FIG. 6. It could be seen that the pellets of phentermine of the 3 formulations all had dissolution rate of 90% or above of the labeled content within 5 min, and thus had desired rapid-release effects.

TABLE 10

Measurement results of dissolution rates of pellets of phentermine

| | Accumulative dissolution percentage of phentermine (%) | | | | |
|---|---|---|---|---|---|
| Formulation number | 5 min | 15 min | 30 min | 45 min | 60 min |
| Formulation 17 | 95.5 | 98.4 | 99.8 | 100.2 | 100.5 |
| Formulation 18 | 92.5 | 99.4 | 100.5 | 100.7 | 100.8 |
| Formulation 19 | 98.2 | 100.5 | 99.2 | 99.8 | 101.2 |

EXAMPLE 12

Preparation of Sustained-Release Pellets of Topiramate

Formulation

| Name of ingredients | Dosage per 10000 preparation units (g) | Dosage ratio (%) (w/w) |
|---|---|---|
| Topiramate | 230 | 36.85 |
| Microcrystalline cellulose (Avicer ® PH102) | 324.9 | 52.05 |
| Methyl cellulose (Methocel™A15LV) | 20.1 | 3.22 |
| Ethyl cellulose | 34.14 | 5.47 |
| Povidone (Povidone K30) | 14.92 | 2.39 |

Preparation Method:

Topiramate as main drug and microcrystalline cellulose as filling agent in the formulation amounts passed through sieve and mixed homogeneously; 70% ethanol was used to dissolve methyl cellulose (Methocel™A15LV) to obtain a solution as binding agent with a suitable concentration, and then used to form soft material; the soft material was placed in an extruder using a certain mesh sieve and extrusion rate to extrude rod like granules; the extruded granules were placed in a spheronizator and spheronized under certain spheronization speed for 3-5 min, the obtained pellets were dried in oven at 40° C. for 2 h to obtain topiramate drug-loaded pellet cores.

The formulation amounts of ethyl cellulose and Povidone (Povidone K30) were weighed, added with 820 ml of 95% ethanol, stirred and dissolved to form a sustained-release coating solution. The prepared topiramate drug-loaded pellet cores aforementioned were placed in a fluidized bed bottom spray coating pan, and the inlet air temperature was set at 40-45° C. (to keep pan internal temperature at 30-35° C.); inlet air pressure was 0.35 bar; atomization pressure was 1.5 bar; solution spray rate was 3-12 g/min. The sustained-release coating solutions was sprayed on surface of drug-loaded pellet cores when the drug-loaded pellets were in fluidization state, to obtain sustained-release pellets of topiramate, and the weight gain from the sustained-release coating was 6.68%.

EXAMPLE 13

Preparation of Sustained-Release Pellets of Topiramate 500 g of the topiramate drug-loaded pellet cores prepared according to Formulation 1 in Example 1, of which drug layer contained binding agent HPMC, was weighed, and placed in a fluidized bed bottom spray coating pan. 720 ml of 95% ethanol was used to prepare sustained-release coating solution containing 30 g of ethyl cellulose and 10 g of PVP K30 respectively. The inlet air temperature was set at 40-45° C. (to keep pan internal temperature at 30-35° C.); inlet air pressure was 0.35 bar; atomization pressure was 1.5 bar; solution spray rate was 3-12 g/min. The sustained-release coating solution was sprayed on surface of drug-loaded pellets in manner of bottom spray when the drug-loaded pellets were in fluidization state, to obtain sustained-release pellets of topiramate with a drug layer containing binding agent HPMC, and the weight gain from the sustained-release coating was 6.86%.

EXAMPLE 14

Preparation of Phentermine-Topiramate Pellet Capsules

The sustained-release pellet of topiramate as prepared in Example 12 and the phentermine pellet as prepared according to Formulation 19 in Example 11 were homogeneously mixed in certain weight ratio via content calculation, and then filled into capsules so that each capsule contained 23 mg of topiramate and 4.67 mg of phentermine hydrochloride (corresponding to 3.75 mg of phentermine).

EXAMPLE 15

Preparation of Phentermine-Topiramate Pellet Capsules

The sustained-release pellet of topiramate as prepared in Example 13 and the phentermine pellet as prepared according to Formulation 19 in Example 11 were homogeneously mixed in certain weight ratio via content calculation, and then filled into capsules so that each capsule contained 23 mg of topiramate and 4.67 mg of phentermine hydrochloride (corresponding to 3.75 mg of phentermine).

EXAMPLE 16

Preparation of Phentermine-Topiramate Pellet Capsules

The first batch of sustained-release pellet of topiramate as prepared in Example 6 and the phentermine pellet as prepared according to Formulation 19 in Example 11 were homogeneously mixed in certain weight ratio via content calculation, and then filled into capsules so that each capsule contained 23 mg of topiramate and 4.67 mg of phentermine hydrochloride (corresponding to 3.75 mg of phentermine).

EXAMPLE 17

Studying on Stability of Phentermine-Topiramate Pellet Capsules

Samples of capsules of Example 14, Example 15, and Example 16 were placed nakedly in sealed dryer with saturated NaCl solution, then the dryer was placed in high temperature (60° C.) oven, acceleration conditions of high temperature and high humidity 5th (60° C., RH75%) were set, and samples were taken on the $0^{th}$, $5^{th}$ and $10^{th}$ day respectively.

The content of pellet sample was poured out, placed in 10 mL volumetric flask, dissolved with suitable amount of methanol under ultrasonic waves, then diluted with water in 5 times volume to reach scale, so that the concentration of main drug was about 5 mg/ml, 0.45 μm organic microfiltration membrane was used for filtration, primary filtrate was discarded, and the subsequent filtrate were used as test solutions. High performance liquid chromatography (Appendix V D, Part II, Chinese Pharmacopoeia, 2010 Edition) was used, octylsilane-bonded silica gel was used as packing agent, column temperature was 35° C., 40% methanol was mobile phase, differential refractive detector was used, and flow rate was 1.5 ml per minute. 200 μl of the test solution was taken and injected in liquid chromatography, chromatogram was recorded until 3 times of the time period of the retention time of main peak, and if the test solution had peaks of impurities, the total content of impurities was calculated by peak area normalization method, and the results were shown in Table 11. It could be seen that the samples (the coating type drug-loaded pellet cores in which the topiramate drug layer was free of binding agent, sample of Example 16) as disclosed in the present invention had stability superior to the matrix type drug-loaded pellet cores (sample of Example 14) and the coating type drug-loaded pellet cores (sample of Example 15) which all contained binding agent in topiramate drug layer.

TABLE 11

Results of stability of phentermine-topiramate pellet capsules

| Sample of stability | Degradation products (relevant substances) (%) | | |
|---|---|---|---|
| | $0^{th}$ day | $5^{th}$ day | $10^{th}$ day |
| Sample of Example 14 | 0.15 | 0.37 | 0.55 |
| Sample of Example 15 | 0.15 | 0.38 | 0.57 |
| Sample of Example 16 | 0.15 | 0.21 | 0.28 |

EXAMPLE 18

Studying on In Vivo Pharmacokinetics of Phentermine-Topiramate Pellets

Test samples: the first batch of topiramate drug-loaded pellet core (immediate-release pellet) as prepared in Example 6 was used as reference preparation, and the first batch of sustained-release pellet of topiramate as prepared in Example 6 was used as test preparation. Administration dose was both 23 mg expressed in topiramate as main drug.

Test subjects: 6 Beagles, 3 male and 3 female, the body weight of Beagles was 8.97±1.05 kg.

Dosage regimen: 6 Beagles were subjected to double cycle random crossover test design, separately orally administrated for once with equivalent dose of the test preparation containing 23 mg of topiramate as main drug and the reference preparation containing 23 mg of topiramate as main drug, an washout period with interval time of 15 days was set between the two cycles. Blood samples (2 mL) were separately taken from leg veins of the Beagles at 0.5, 1, 2, 3, 4, 6, 8, 10, 12, 16, 24, 36, 48 h, respectively, after administration, placed in negative pressure glass tubes treated with heparin sodium, centrifuged at 4000 r/min for 10 min to separate plasma, 1 ml of the plasma was moved to EP tube, labeled with test number, random number of Beagle and blood sampling time, and the blood samples were kept at −20° C. for treatment and analysis.

Plasma sample treatment: 100 μL of plasma of Beagle after administration was taken, placed in 1.5 ml centrifuge tube, added with 20 μl of water, added with 20 μl of internal standard solution (500 ng/ml Nimesulide solution), added with 0.5 ml of methanol as precipitator, subjected to eddy for 3 min, centrifuged for 10 min (9500 rpm), supernatants (20 μl) were separately sucked up, and analyzed with LC/MS/MS under the following chromatography conditions, and the chromatograms were recorded.

Chromatography conditions: analysis column was Zorbax C8, 5 μm particle size, 150×4.6 mm I.D., Agilent Company of US; pre-column was C18 protection column, 4×3.0 mm I.D., Phenomenex Company, USA; column temperature was 25° C.; mobile phase was methanol-0.5 mM ammonium acetate (75:25, v/v); flow rate was 0.5 mL/min; internal standard was Nimesulide (500 ng/mL).

Mass spectrometric conditions: API 3000 type tandem quadrupole mass spectrometer. Ion source was atmospheric chemical ion source (Turbo Ionspray source); detection was performed in negative ion manner; ejection voltage was −4200 V; source temperature was 450° C.; nebulizer gas (NEB) was 8; curtain gas (CUR) was 11; collision gas (CAD) was 5; scanning manner was multiple reaction monitoring (MRM), the ion reactions for quantitative analysis were separately: m/z 338→m/z 78 (topiramater, CE—55 V), m/z 307→m/z 229 (internal standard nimesulide, CE—20 V); scanning time was 150 msec.

Pharmacokinetic data processing method: plasma concentration data were analyzed with DAS 2.0 analytic software.

Figure 5:
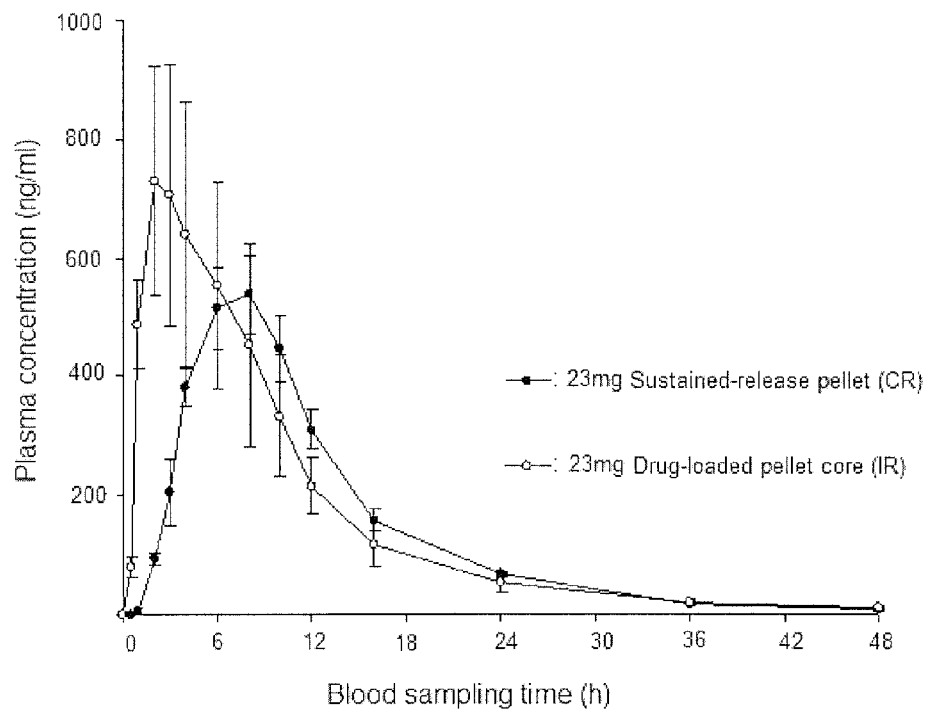
FIG. 5 shows in vivo plasma concentration curves of the sustained-release pellet of topiramate of the present invention.

Results of measurement: after Beagles were orally administered with equivalent dose (23 mg) of reference preparation (the first batch of topiramate drug-loaded pellet cores of Example 6) and test preparation (the first batch of sustained-release pellet of topiramate of Example 6), average plasma concentrations (μg/ml) at different time points were shown in FIG. 5, and main pharmacokinetic parameters were shown in Table 12.

TABLE 12

Main pharmacokinetic parameters

| Test sample | $T_{max}$ (h) | $C_{max}$ (μg · ml$^{-1}$) | $AUC_{0-Tn}$ (h · μg · ml$^{-1}$) | Relative bioavailability (%) |
|---|---|---|---|---|
| reference preparation | 2.33 ± 0.47 | 1.11 ± 0.13 | 9.39 ± 3.23 | 100.00% |
| Test preparation | 7.33 ± 0.94 | 0.55 ± 0.07 | 8.72 ± 2.67 | 92.87% |

The results of FIG. 5 and Table 12 showed that the Beagles orally administered with the sustained-release composition of topiramate as provided by the present invention (the first batch of sustained-release pellets of topiramate of Example 6, containing 23 mg of topiramate) showed significantly extended $T_{max}$, significantly decreased $C_{max}$, in comparison with the immediate-release topiramate drug-loaded pellet cores (reference preparation, the first batch of topiramate pellet cores of Example 6, containing 23 mg of topiramate), and more important, the relative bioavailability of the test preparation was 92.87% of that of the reference preparation. this indicated that the topiramate sustained-release composition as provided by the present invention had biologically equivalent to the reference preparation, and showed significant features of sustained-release preparation, that was, the peak concentration decreased significantly, and the action time was significantly extended.

Although the specific models of the present invention have been described in details, those skilled in the art would understand that these details can be modified or changed according to all teachings of disclosures in the art, and all these changes fall into the protection scope of the present invention. The total scope of the present invention is given by the appended claims and any equivalents thereof.

What is claimed is:

1. A combination product, which comprises phentermine or salt thereof, and sustained-release pellet of topiramate, wherein the sustained-release pellet of topiramate comprises a blank pellet core, a drug layer and a sustained-release coating layer, wherein the drug layer is free of binding agent selected from the group consisting of starch slurry, syrup, polyvinylpyrrolidone, methyl cellulose (MC), ethyl cellulose (EC), highly-substituted hydroxypropyl cellulose (H-HPC), hydroxypropyl methyl cellulose (HPMC), sodium carboxymethyl cellulose, gelatin, Arabic gum, and a mixture thereof.

2. The combination product of claim 1, wherein the sustained-release coating layer comprises a sustained-release material selected from ethyl cellulose, Eudragit NE 30D, Eudragit RS 30D, Eudragit RL30D, and a mixture thereof.

3. The combination product of claim 1, wherein the sustained-release coating layer comprises ethyl cellulose and PVP K30.

4. The combination product of claim 3, wherein the weight ratio of ethyl cellulose to PVP K30 is (1:0.20)-(1:0.45).

5. The combination product of claim 1, wherein the weight gain from the sustained-release coating is 2%-30%.

6. The combination product of claim 1, wherein the drug layer of sustained-release pellet of topiramate consists of topiramate.

7. The combination product of claim 1, wherein the blank pellet core has a particle size of 150 μm-1500 μm.

8. The combination product of claim 1, wherein the dosage form of said phentermine or salt thereof is immediate re ease pellet.

9. The combination product according to claim 1, which is a capsule or tablet.

10. A method for preparing the sustained-release pellet of topiramate in the combination product according to claim 1, the method comprising:

a) dissolving ingredients of the drug layer with suitable amount of solvent to form a drug solution, and coating the blank pellet core with the drug solution to give a drug-loaded pellet;

b) coating the drug-loaded pellet obtained in step a) with ingredients of the sustained-release coating layer.

11. The method according to claim 10, wherein the step b) comprises the following steps:

dissolving ingredients of the sustained-release coating layer in a solvent, and coating the drug-loaded pellet obtained in step a) with the resultant solution.

12. The preparation method of claim 10, wherein the solvent is water, ethanol, acetone, propylene glycol, chloroform or a mixture thereof.

13. A method for realizing weight loss, blood fat reduction, antihypertension or treatment of mental or nervous diseases in a subject, comprising a step of administering the subject in such need a therapeutically effective amount of the combination product according to claim 1.

14. The combination product of claim 3, wherein the weight ratio of ethyl cellulose to PVP K30 is (1:0.25)-(1:0.40).

15. The combination product of claim 3, wherein the weight ratio of ethyl cellulose to PVP K30 is (1:0.30)-(1:0.35).

16. The combination product of claim 1, wherein the weight gain from the sustained-release coating is 3%-20%.

17. The combination product of claim 1, wherein the weight gain from the sustained-release coating is 5%-15%.

18. The combination product of claim 1, wherein the weight gain from the sustained-release coating is 5%-10%.

19. The combination product of claim 1, wherein the weight gain from the sustained-release coating is 5%-8%.

20. The combination product of claim 1, wherein the weight gain from the sustained-release coating is 6%-8%.

21. The combination product of claim 1, wherein the blank pellet core has a particle size of 250 μm-1000 μm.

22. The combination product of claim 1, wherein the blank pellet core has a particle size of 300 μm-900 μm.

23. The combination product of claim 1, wherein the blank pellet core has a particle size of 400 μm-850 μm.

24. The combination product of claim 1, wherein the blank pellet core has a particle size of 610 μm-750 μm.

25. The preparation method of claim 10, wherein the solvent is a mixture of water and ethanol.

* * * * *